United States Patent

Kume et al.

[11] Patent Number: 5,563,264
[45] Date of Patent: Oct. 8, 1996

[54] PREPARATION OF βLACTAM COMPOUNDS

[75] Inventors: Masaharu Kume, Neyagawa; Tadatoshi Kubota, Habikino, both of Japan

[73] Assignee: Shionogi & Co., Ltd., Osaka, Japan

[21] Appl. No.: 423,725

[22] Filed: Apr. 18, 1995

Related U.S. Application Data

[63] Continuation-in-part of Ser. No. 190,608, Feb. 2, 1994, abandoned.

[30] Foreign Application Priority Data

Feb. 10, 1993 [JP] Japan .................................. 5-022451
Aug. 5, 1994 [JP] Japan .................................. 6-184490

[51] Int. Cl.⁶ .................. C07D 463/00; C07D 477/00; C07D 501/08; C07D 499/06
[52] U.S. Cl. .................. 540/205; 540/200; 540/214; 540/215; 540/300; 540/301; 540/302; 540/357; 540/364
[58] Field of Search .................. 540/205, 215, 540/300, 301, 302

[56] References Cited

U.S. PATENT DOCUMENTS 4,122,086  10/1978  Hall ........................ 260/306.7

FOREIGN PATENT DOCUMENTS 0528678  2/1993  European Pat. Off.

OTHER PUBLICATIONS

Moriarty, Zet. Letters 34, 4129 (1993).
Kalogiannis et al., The Journal of Organic Chemistry, vol. 55, No. 17 (1990) pp. 5041–5044.
Fairfax et al., Journal of The Chemical Society, Perkin Transactions 1, No. 21 (1992) pp. 2837–2844.

*Primary Examiner*—Mark L. Berch
*Attorney, Agent, or Firm*—Wenderoth, Lind & Ponack

[57] ABSTRACT

A process for preparing a β-lactam compound of the formula (I):

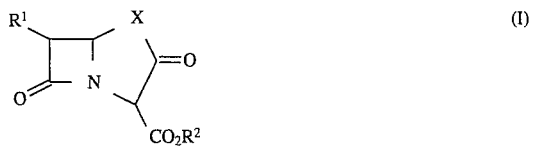

which comprises cyclization, in the presence of a catalyst, of an azetidinone derivative of the formula:

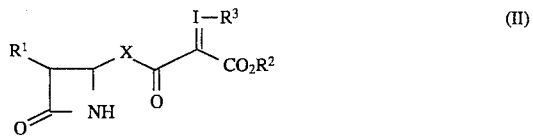

is provided in which $R^1$ is hydrogen, alkyl which is optionally substituted, or amino which is optionally substituted; $R^2$ is a carboxy-protecting group; and X is alkylene which is optionally intervened by —O— or —S—, and/or which is optionally substituted; and $R^3$ is aryl which is optionally substituted. The catalyst is preferably a transition metal salt (especially rhodium) or is an acid.

10 Claims, No Drawings

PREPARATION OF βLACTAM COMPOUNDS

This is a continuation-in-part application of U.S. Ser. No. 08/190,608 filed on Feb. 2, 1994 now abandoned.

FIELD OF THE INVENTION

The present invention relates to a useful process for preparing β-lactam antibiotics, and specifically to a process for preparing carbapenam derivatives, which are useful intermediates for preparation of β-lactam antibiotics, as well as intermediates which are useful for the process. More specifically, the present invention relates to a process for preparation of β-lactam antibiotics which comprises cyclization of novel and useful azetidinone derivatives, as well as such azetidinone derivatives.

Prior Art

Currently, β-lactam antibiotics are clinically used in treatment of infections. The β-lactam antibiotics may be classified, and include antibiotics having carbapenam or carbapenem nucleus, which belong to newer types of antibiotics.

A process for preparation of carbapenam or carbapenem antibiotics may involve a process which comprises making derivatives having carbapenam nucleus from azetidinone derivatives. Such process is described in EP 0037080 A1, and is as shown below:

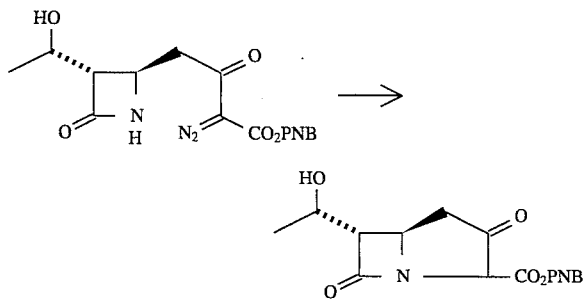

This process involves cyclization which comprises heating the diazo compound at 50°–100° C., and preferably heating in the presence of catalyst, $CuSO_4$, $Pd(OAc)_2$, or $Rh_2(OAc)_4$. To date, the process has been utilized industrially at large scale.

However, the above process is disadvantageous in that the azide reagent and the diazo compound used in the process are explosive while they are heating. In other words, it is very dangerous to treat a large amount of the diazo compound. Accordingly, the above process is not desired as industrial process for preparation of carbapenem antibiotics.

Thus, the applicants have studied and found a safe and convenient process for preparation of carbapenem antibiotics, which does not comprise using the above azide reagent and diazo compound.

Description of the Invention

The present invention relates to a process for preparing a β-lactam compound of the formula (I):

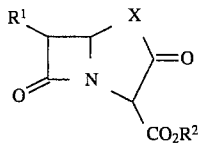

in which $R^1$ is hydrogen, alkyl which is optionally substituted, or amino which is optionally substituted;

$R^2$ is a carboxy-protecting group; and

X is alkylene which is optionally intervened by —O— or —S—, and/or which is optionally substituted.

which comprises cyclization of an azetidinone derivative of the formula:

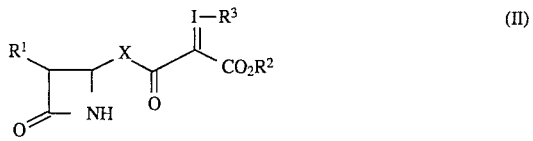

wherein $R^1$, $R^2$, and X are as defined above, and $R^3$ is aryl which is optionally substituted.

In the above formula, the term "alkyl" in the definition of $R^1$ refers to a straight or branched $C_1$–$C_6$ alkyl group, and preferably refers to a straight or branched $C_1$–$C_4$ alkyl group. Substituents on the alkyl are exemplified by halogen, hydroxy which may be substituted by a hydroxy-protecting group, and so on. The protecting groups of hydroxy include, for example, (lower alkoxy)carbonyl such as $C_1$–$C_4$ alkoxycarbony (for example, t-butyloxycarbonyl), halogenated (lower alkoxy) carbonyl such as halogenated ($C_1$–$C_3$) alkoxycarbonyl (for example, 2-iodoethyloxycarbonyl, 2,2,2-trichloroethyloxycarbony), aryl (lower alkoxy) carbonyl such as phenyl ($C_1$–$C_4$) alkoxycarbony of which benzene ring may have substituent(s) (for example, benzyloxycarbonyl, o-nitrobenzyloxycarbony, p-nitrobenzyloxycarbonyl, p-methoxybenzyloxycarbonyl), tri-(lower alkyl)silyl such as tri-($C_1$–$C_4$)alkylsilyl (for example, trimethylsilyl, t-butyldimethylsilyl), substituted methyl such as $C_1$–$C_4$ alkoxymethyl (for example, methoxymethyl), $C_1$–$C_4$ alkoxy ($C_1$–$C_4$)alkoxymethyl (for example, 2-methoxyethoxymethyl), $C_1$–$C_4$ alkylthiomethyl (for example, methylthiomethyl), tetrahydropyranyl, and the like conventional groups. Preferably, $R^1$ is hydroxyethyl.

Substituent on amino group of $R^1$ is preferably amino-protecting group having 1 to 20 carbon atoms which can be removed without any inconvenient changes in any other moiety on the molecule, and which have been used in the field of penicillin and cephalosporin. Typical substituents include an alkyl having 1 to 8 carbon atoms (t-butyl, methoxymethyl, methoxyethoxymethyl, trichloroethyl, tetrahydropyranyl, and so on), an aralkyl having 7 to 20 carbon atoms (benzyl, diphenylmethyl, trityl, methoxybenzyl, nitrobenzyl, methylbenzyl, and so on), an arylthio having 6 to 12 carbon atoms (nitrophenylthio, and so on), an alkylidene having 1 to 8 carbon atoms, an aralkylidene having 7 to 14 carbon atoms (benzylidene, or substituted benzylidene), an acyl [alkanoyl having 1 to 8 carbon atoms (formyl, acetyl, chloroacetyl, trichloroacetyl, trifluoroacetyl, and so on), an aralkanoyl having 7 to 15 carbon atoms (phenylacetyl, phenylglycyl, phenylglycosyl, phenylmaronyl, thiazolylacetyl, aminothiazolyl-α-hydroxyiminoacetyl, and so on), an aroyl having 7 to 15 carbon atoms (benzoyl, nitrobenzoyl, and so on), an alkoxycarbonyl having 2 to 12 carbon atoms (in which the alkyl moiety is methyl, ethyl, propyl, cyclopropylethyl, isopropyl, butyl, pentyl, hexyl, isobutyl, trichloroethyl, pyridylmethyl, cyclopentyl, cyclohexyl, and so on), an aralkoxycarbonyl having 8 to 15 carbon atoms (in which the aralkyl moiety is benzyl, diphenylmethyl, nitrobenzyl, and so on), a dibasic acid acyl having 3 to 10 carbon atoms (succinyl, phthaloyl, and so on), a halosulfonyl, a phosphate acyl having 0 to 10 carbon atoms (dialkoxyphophoryl, dichlorophophoryl), and so on], a trialkylsilyl having, 3 to 15 carbon atoms, a trialkylstannyl having 3 to 15 carbon atoms, and so on, each of which groups may be further substituted.

In the above formula, the term "carboxy-protecting group" in $R^2$ refers, for example, to lower alkyl such as $C_1$–$C_4$ alkyl (for example, methyl, ethyl, isopropyl, t-butyl), halogenated lower alkyl such as $C_1$–$C_3$ alkyl (for example, 2-iodoethyl, 2,2,2-trichloroethyl), lower alkoxymethyl such as $C_1$–$C_4$ alkoxymethyl (methoxymethyl, ethoxylmethyl, isobutoxymethyl), lower aliphatic acyloxymethyl such as $C_1$–$C_5$ alkanoyloxymethyl (for example, acetoxymethyl, propionyloxymethyl, butyryloxymethyl, pivaloyloxymethyl), lower alkoxycarbonyloxyethyl such as 1-($C_1$–$C_4$ alkoxycarbonyloxy)ethyl (for example, 1-methoxycarbonyloxyethyl, 1-ethoxycarbonyloxyethyl), a lower alkenyl which may be substituted, such as $C_3$–$C_{10}$ alkenyl which may be substituted by $C_1$–$C_4$ alkyl or phenyl (for example, allyl, 2-methylallyl, 3-methylallyl, 3-phenylallyl), monoaryl(lower)alkyl which may be substituted, such as phenyl ($C_1$–$C_4$) alkyl of which benzene ring may be substituted by $C_1$–$C_4$ alkoxy, nitro, halogen, and so on (for example, benzyl, p-methoxybenzyl, 2,4-dimethoxybenzyl, o-nitrobenzyl, p-nitrobenzyl, p-chlorobenzyl), di-aryl(lower)alkyl which may be substituted, such as diphenyl($C_1$–$C_4$) alkyl which may be substituted by $C_1$–$C_4$ alkoxy and so on (for example, diphenylmethyl, di-p-anisylmethyl), an aryl such as phenyl which may be substituted by halogen, nitro, $C_1$–$C_4$ alkoxy, and so on (for example, phenyl, p-chlorophenyl, 2,4,5-trichlorophenyl, p-nitrophenyl, o-nitrophenyl, p-methoxyphenyl), a heteroaryl such as pyridyl or pyrimidyl which may be substituted by $C_1$–$C_4$ alkyl (for example, 2-pyridyl, 3-pyridyl, 4-pyridyl, 2-pyrimidyl, 2-(4, 6-dimethyl)pyrimidyl), phthalydyl, and the like conventional groups which will protect the carboxy group.

In the above formula, "an aryl" in $R^3$ includes phenyl, naphthyl, which may be substituted by halogen, lower alkyl, lower alkoxy, hydroxy, amino, nitro, and so on. Particularly preferred group is phenyl.

An "alkylene" in the definition of X includes preferably $C_1$–$C_5$ alkylene, more preferably X includes $C_1$–$C_3$ alkylene, and exemplified by methylene, ethylene, propylene, butylene, and pentylene. This alkylene can be intervened by —O—, or —S—, and/or be substituted by a substitituent (e.q. lower alkyl, lower alkoxy, lower alkylthio, aryl, lower alkenyl, etc.). This includes —OCH$_2$—, —SCH$_2$—, —O(CH$_2$)$_2$—, —S(CH$_2$)$_2$—, or a group of the formula:

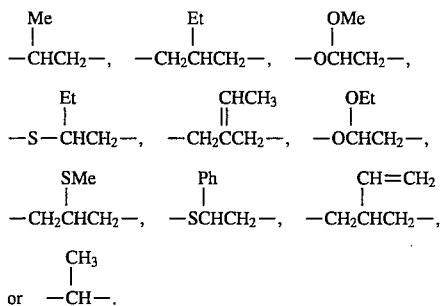

One of the preferred groups is an "alkylidene group" of the formula:

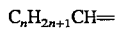

wherein n is an integer which is equal to or above 0, and preferably, an integer of 0 to 5. The alkylidene includes ethylidene (CH$_3$CH=), propylidene (CH$_3$CH$_2$CH=), isopropylidene ((CH$_3$)$_2$C=), and so on. Preferably, the alkylidene is ethylidene.

The process of the present invention involves the step which comprises synthesizing β-lactam compounds from azetidinone derivatives. The reaction of the process is conducted in a solvent which does not afford an adverse effect to the reaction, and preferably in an alcoholic solvent (for example, methanol, ethanol, isopropyl alcohol), a halogenated hydrocarbon (for example, methylene chloride), acetone, nitrils (for example, acetonitrile), or other aprotic solvent (for example, benzene, toluene, tetrahydrofuran).

The reaction is substantially completed within several ten minutes to several ten hours at −80° C. to 100° C., preferably at −40° C. to 50° C., and most preferably under ice-cooling to at room temperature.

The present process is preferably conducted in the presence of a catalyst. The catalyst may effect cyclization of the compound (II). Preferably, the catalyst includes transition metals, and in particular rhodium salts. The rhodium salts include a salt forming with a carboxylic acid, and specifically include acetate (Rh$_2$(OAc)$_4$), trifluoroacetate (Rh$_2$(CF$_3$CO$_2$)$_4$), pivalate (Rh$_2$((CH$_3$)$_3$CCO$_2$)$_4$), and octanate (Rh$_2$(C$_7$H$_{15}$COO)$_4$). The amount of the catalyst varies depending on kinds of the used catalyst, reaction temperature, and so on, and preferably, the amount is 0.001 to 0.1 mole per mole of azetidinone derivative.

Further, an acid may be selected as the catalyst in the reaction. Such acid comprises an acid which can effect the cyclization of the compound (II), and preferably, sulfonic acids (for example, methanesulfonic acid, p-toluenesulfonic acid), sulfuric acid, nitric acid, perchloric acid, periodic acid, boron trifluoride. An amount of the acid varies depending on kinds of the used acid, reaction temperature, and so on, and preferably, the amount is 0.001 to 0.1 mole per mole of azetidinone derivative.

Altanatively, it is understood that the reaction of the present invention can be conducted by dissolving the azetidinone derivative of the formula (II) in the alcoholic solvents as stated above, and treating the solution with a resin of sulfonate type.

According to other embodiment, the present invention provides a novel azetidinone derivative of the formula (II):

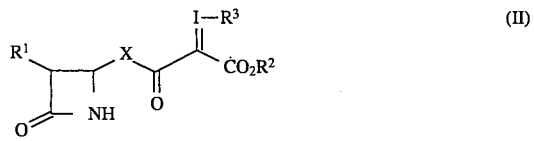

wherein $R^1$, $R^2$, $R^3$, and X are as defined above. The azetidinone derivative is produced by reacting a compound of the formula (III):

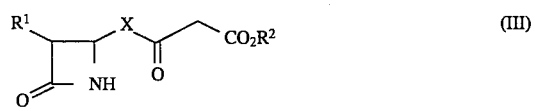

wherein $R^1$, $R^2$, and X are as defined above, with a compound of the formula:

wherein $R^3$ is as defined above, and Q is a substituent derived from an anion part of an acid.

In the formula: $R^3$—I(Q)$_2$, Q is a substituent derived from an anion part of an acid including an organic acid, and an inorganic acid. The organic acid includes carboxylic acids and sulfonic acids. The inorganic acid includes halogenated hydro-acids such as HF, HCl, HBr. A preferred compound of $R^3$—$I(Q)_2$ includes $PhI(OCOCH_3)_2$, $PhI(OCOCF_3)_2$, $PhIF_2$. The reaction of the process is conducted in a solvent in the presence of a base. The solvents include ones which do not afford an adverse effect to the reaction, and preferably the solvent is an alcoholic solvent such as methanol. An organic base (tertiary amine, aromatic base), or an inorganic base (oxides of alkali metals or alkaline earth metals, hydroxides, carbonates, bicarbonates, and so on) can be used as the base.

The compound of the formula (III) can be produced according to the known method in the art of β-lactam antibiotics.

The compound of the formula (II) also can be produced using $(PhIO)n$, $PhI(OH)OTs$, etc. instead of $R^3$—$I(Q)_2$ according to the method of the literature [Varvoglis A., Synthesis, 709 (1984), and Moriarty R. H., Valid R. K., Synthesis, 431 (1990)].

The present invention provides a process for preparing a β-lactam compound of the formula (I) via the azetidinone derivative of the formula (II), and specifically a process for preparing a β-lactam compound of the formula (I):

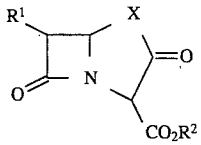

in which $R^1$, $R^2$, and X are as defined above;
which comprises reacting a compound of the formula (III):

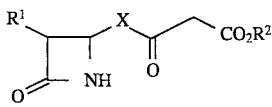

wherein $R^1$, $R^2$, and X are as defined above, with a compound of the formula:

$R^3$—$I(Q)_2$ wherein $R^3$ is as defined above to give the azetidinone derivative of the formula:

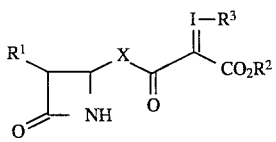

wherein $R^1$, $R^2$, $R^3$, and X are as defined above and then, the latter derivative is cyclized.

Further, the present invention provides a process for preparing a β-lactam compound of the formula (I) via two steps from the compound (III), which is the starting material of the azetidinone derivative of the formula (II), and specifically a process for preparing a β-lactam compound of the formula (I):

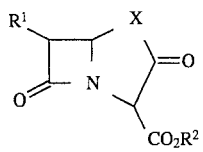

in which $R^1$, $R^2$, and X are as defined above;
which comprises reacting a compound of the formula (III):

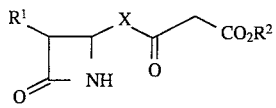

wherein $R^1$, $R^2$, and X are as defined above, with a compound of the formula:

$R^3$—$I(Q)_2$ wherein $R^3$ is as defined above, or with $(PhIO)n$, $PhI(OH)OTs$ wherein Ph is phenyl, n is an integer, Ts is a residue of p-toluenesulfonate ester (First step), and then, adding an acid to the reaction (Second step). In this reaction, the compound (II), which is believed to be a major intermediate in the reaction of the first step, may or may not to be isolated. In the latter case, the acid can be added directly to the reaction containing the compound (II) to proceed the cyclization reaction.

The compound of the formula (I) obtained from the process of the present invention can be used as starting material for the compound of the formula:

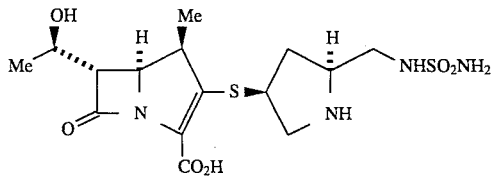

, which is described, for example, in the Japanese Patent Application No. 221767/1992. For example, the compound (I) is esterified by reacting with phosphate to give an activated compound, which is reacted with a thiol compound to give 2-thio-carbapenem compound; or chlorinated to give a 3-chloro-carbacephem compound.

EXAMPLES

The present invention is illustrated in more detail by the following Examples and Reference Example, but should not be construed to be limited to the scope of the present invention.

EXAMPLE 1

Diphenylmethyl (1R, 5R, 6S)-6-[(R)-1-hydroxyethyl]-1-methyl-2-oxo-1-carbapenam-3-carboxylate (compound 3)

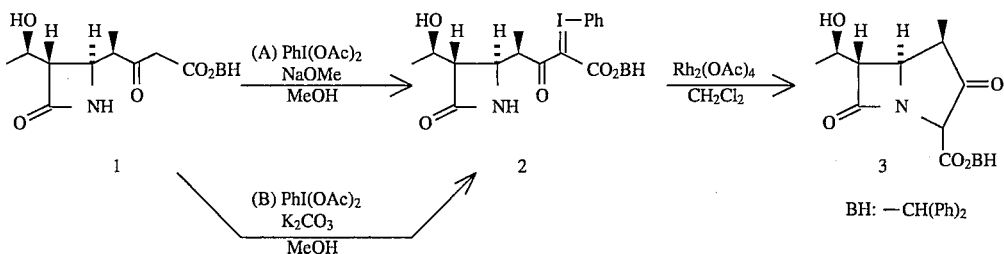

I. (3S,4R)-3-[(R)-1-hydroxyethyl]-4-[(R)-3-diphenylmethoxycarbonyl-1-methyl-2-oxo-3-phenyliodoniopropyl]-azetidin-2-one (compound 2)

Method A

Iodobenzene diacetate (1.68 g, 5.22 mmole) was dissolved in 20 ml of methanol, and 1.26N solution of sodium methylate (8.28 ml, 10.4 mmole) was added thereto, and the mixture was stirred at room temperature for 10 minutes. Then, compound 1: (3S,4R)-3-[(R)-1-hydroxyethyl]-4-[(R)-3-diphenylmethoxycarbonyl- 1-methyl-2-oxopropyl]-azetidin-2-one (2.00 g, 5.06 mmole) was added thereto, and the resultant mixture was stirred at room temperature for 20 minutes. The reaction mixture was concentrated, and ethyl acetate (30 ml) was added to the residue, and then the precipitated sodium acetate was filtered off. The filtrate was concentrated, and ethyl acetate (10 ml) and hexane (40 ml) were added to the residue. The resultant crystals were filtered to yield compound 2 (2.70 g, 89%) as a pale yellow crystal.

Method B

Iodobenzene diacetate (420 mg, 1.30 mmole) was dissolved in 5 ml of methanol, and potassium carbonate (180 mg, 1.30 mmole) was added thereto, and the mixture was stirred at room temperature for 10 minutes. Then, compound 1 (500 mg, 1.27 mmole) was added thereto, and the resultant mixture was stirred at room temperature for 20 minutes. The reaction mixture was concentrated, and ethyl acetate (8 ml) was added to the residue, and then the precipitated potassium acetate was filtered off. The filtrate was concentrated, and ethyl acetate (4 ml) and hexane (20 ml) were added to the residue. The resultant crystals were filtered to yield compound 2 (702 mg, 93%) as a pale yellow crystal.

Compound 2: mp;109°–111° C. $^1$H-NMR(CDCl$_3$) δ: 7.66 (2H, d, J=8.2Hz), 7.53 (1H, t, J=8.2Hz), 7.4–7.2 (12H,m), 6.86 (1H,s), 6.05 (1H, brs), 4.14–3.88 (2H, m), 3.77 (1H, dd, J=1.8Hz, 8.3Hz), 2.69 (1H, dd, J=1.8Hz, 8.8Hz), 1.26 (3H, d, J=6.4Hz), 1.20 (3H, d, J=6.8Hz); IR (CHCl$_3$) cm$^{-1}$: 3400 (br), 1752, 1655, 1560, 1545, 1538, 1380, 1370, 1340.

II. The title compound 3

To the suspension which had been prepared by suspending compound 2 obtained in the step I (200 mg, 0.335 mmole) in 6 ml of dichloromethane, was added rhodium acetate (1.5 mg, 0.0034 mmole), and the mixture was stirred at room temperature for 20 minutes. The reaction mixture was diluted with dichloromethane, and the dilution was washed once with water, once with brine, dried over anhydrous sodium sulfate, and concentrated. The resultant residue was purified by chromatography (using toluene: ethyl acetate: acetic acid=250:250:1 as an eluent) to yield 113 mg of compound 3 as a colorless foam (86%).

Compound 3: $^1$H-NMR (CDCl$_3$) δ: 7.4–7.2 (10H, m), 6.87 (1H, s), 4.76 (1H, s), 4.29 (1H, quintet, J=6.5Hz), 4.22 (1H, dd, J=2.3Hz, 7.9Hz), 3.24 (1H, dd, J=2.3Hz, 7.0Hz), 2.77 (1H, quintet, J=7.7Hz), 1.37 (3H, d, J=6.2Hz), 1.20 (3H, d, J=7.8Hz); IR (CHCl$_3$) cm$^{-1}$: 3600, 3500 (br), 1765, 1750 (shoulder), 1495, 1455, 1380, 1360, 1295.

EXAMPLE 2

The same compound as that of Example 1

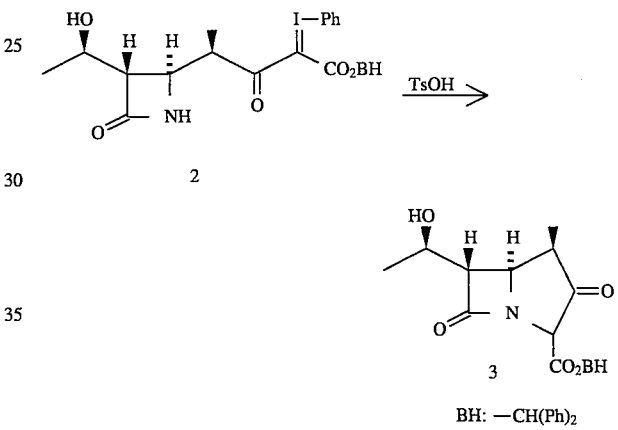

Compound 2 (200 mg, 0.335 mmole) which was produced by the procedure of step I in Example 1 was suspended in 2 ml of ethanol, 3 mg of P-toluensulfonic acid hydrate (0.016 mmol) was added thereto, and the mixture was stirred at room temperature for 15 minutes. The reaction mixture was concentrated and the residue was purified over chromatography on silica gel (using toulene:ethyl acetate:acetic acid= 250:250:1 as an eluent) to yield 124 mg of compound 3 as a colorless foam (94%).

The NMR and IR data of the resultant compound are the same as those in Example 1.

EXAMPLE 3

The same compound as that of Example 1

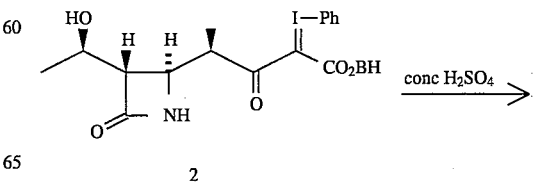

-continued

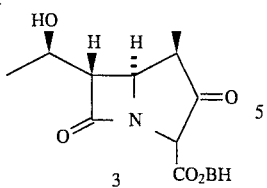

Compound 2 (200 mg, 0.335 mmole) which was produced by the procedure of step I in Example 1 was suspended in 2 ml of ethanol, 1 μl of conc. sulfuric acid was added thereto, and the mixture was stirred at room temperature for 30 minutes. The reaction mixture was diluted with ethyl acetate, and the dilution was washed once with diluted aqueous sodium bicarbonate and once with brine. The organic layer was dried over anhydrous sodium sulfate, and the residue was purified over chromatography on silica gel (using touluene:ethyl acetate:acetic acid=250:250:1 as an eluent) to yield 120 mg of compound 3 as a colorless foam (91%).

The NMR and IR data of the resultant compound are the same as those in Example 1.

EXAMPLE 4

The same compound as that of Example 1

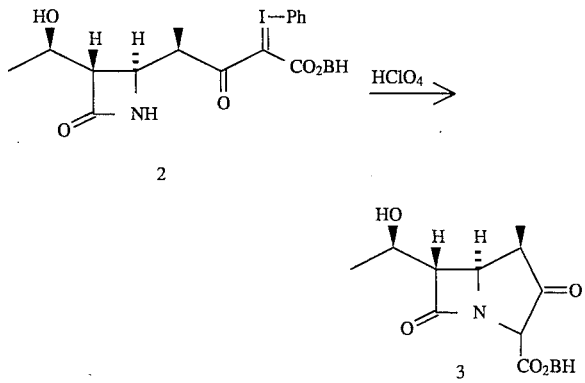

Compound 2 (200 mg, 0.335 mmole) which was produced by the procedure of step I in Example 1 was suspended in 2 ml of ethanol, 1 μl of 70% perchloric acid was added thereto, and the mixture was stirred at room temperature for 2 hours. The reaction mixture was diluted with ethyl acetate, and the dilution was washed once with diluted aqueous sodium bicarbonate and once with brine. The organic layer was dried over anhydrous sodium sulfate, and the residue was purified over chromatography on silica gel (using toluene:ethyl acetate:acetic acid=250:250:1 as an eluent) to yield 119 mg of compound 3 as a colorless foam (90%).

The NMR and IR data of the resultant compound are the same as those in Example 1.

EXAMPLE 5

The same compound as that of Example 1

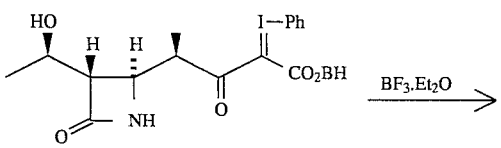

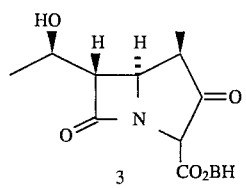

Compound 2 (200 mg, 0.335 mmole) which was produed by the procedure of step I in Example 1 was suspended in 2 ml of ethanol, 1 μl of boron trifluoride-ehter complex was added thereto, and the mixture was stirred at room temperature for 2 hours. The reaction mixture was diluted with ethyl acetate, and the dilution was washed once with diluted aqueous sodium bicarbonate and once with brine. The organic layer was dried over anhydrous sodium sulfate, and the residue was purified over chromatography on silica gel (using toluene:ethyl acetate:acetic acid=250:250:1 as an eluent) to yield 115 mg of compound 3 as a colorless foam (87%).

The NMR and IR data of the resultant compound are the same as those in Example 1.

EXAMPLE 6

The same compound as that of Example 1

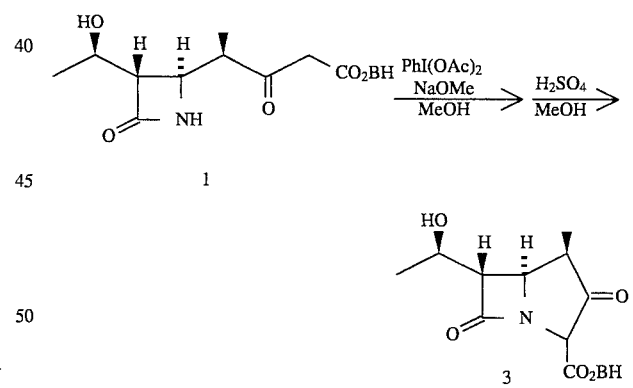

Iodobenzne acetate (168 mg, 0.522 mmole) was dissolved in 2 ml of methanol, to which 1.03M solution of sodium methylate in methanol (1.01 ml, 1.04 mmole) was added and the mixture was stirred at room tempetarure for about 10 minutes. To the mixture was added compound 1 (200 mg, 0.506 mmol) and the mixture was stirrred at room temperture for 20 mitutes. Then, to the reaction mixture was added conc.sulfuric acid (about 40 μl) dropwise until the pH was adjusted to about 1. After completion of the addition, the mixture was stirred at room temperature for about 30 minutes. The reaction mixture was then diluted with ethyl acetate, and the dilution was washed twice with diluted aqueous sodium bicarbonate and once with brine. The organic layer was dried over anhydrous sodium sulfate, concentrated, and the residue was purified over chromatography on silica gel (using toluen:ethyl acetate:acetic acid= 250:250:1 as an eluent) to yield 142 mg of compound 3 as a colorless foam (71%).

The NMR and IR data of the resultant compound are the same as those in Example 1.

EXAMPLE 7 p-Nitrobenzyl (1R, 5R, 6S)-6-[(R)-1-tert-butyldimethylsilyloxyethyl]- 1-methyl-2-diphenylphosphoryloxy-1-carba- 2-penem-3-carboxylate (compound 6)

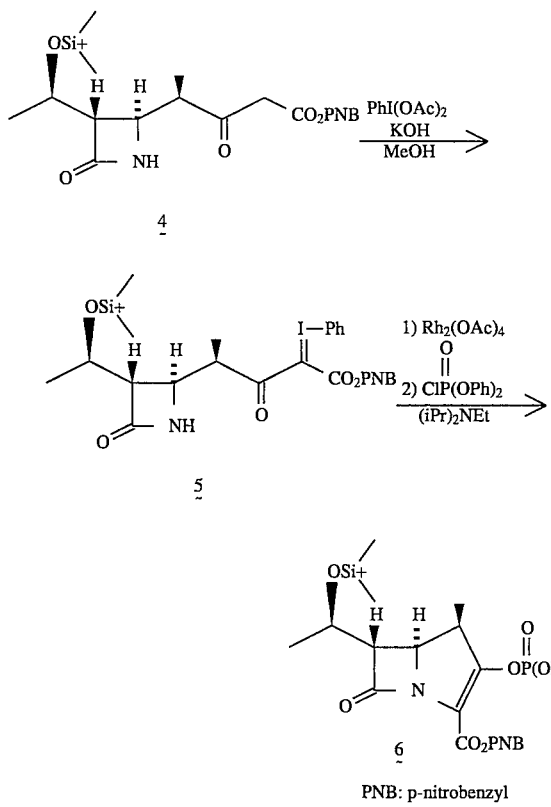

PNB: p-nitrobenzyl

I. (3S, 4R)-3-[(R)-1-tert-butyldimethylsilyloxyethyl]-4-[(R)- 1-methyl-3-p-nitrobenzyloxycarbonyl-2-oxo-3- phenyliodoniopropyl]-azetidin- 2-one (compound 5)

Compound 4, (3S, 4R)-3-[(R)-1-tert-butyldimethylsilyloxyethyl]-4-[(R)-1-methyl-3-p-nitorobenzyloxycarbonyl- 2-oxopropyl]-azetidin- 2-one (500 mg, 1.04 mmole) was dissolved in 1 ml of methanol, and the solution was cooled up to −5 ° C. To the cooled solution were added a solution of potassium hydroxide (136 mg, 2.08 mmole) in 1 ml of methanol, and then, a solution of iodobenzene diacetate (337 mg, 1.05 mmole) in 2 ml of methanol, and the resultant mixture was stirred at −10° to −5 ° C. for 40 minutes. To the mixture was added ice-cold water, and the resultant mixture was extracted twice with dichloromethane. The organic phase was dried over anhydrous sodium sulfate, and then concentrated to yield 606 mg of compound 5 as pale yellow crystals (86%).

Compound 5: $^1$H-NMR (CDCl$_3$) δ: 8.18–8.14 (2H, m), 7.7–7.3 (7H, m), 6.10 (1H, brs), 5.17 (2H, s), 4.36–4.22 (1H, m), 4.22–4.08 (1H, m), 3.86 (1H, dd, J=2.1Hz, 4.1Hz), 3.04–2.97 (1H, m), 1.17 (3H, d, J=6.8Hz), 1.14 (3H, d, J=6.2Hz), 0.84 (9H, s), 0.05 (3H, s), 0.04 (3H, s).

II. The title compound 6

To the solution which had been prepared by dissolving compound 5 obtained above (120 mg, 0.176 mmole) in 1 ml of dichloromethane, was added 8 mg of rhodium acetate (0.018 mmole), and the mixture was stirred for 20 minutes. The reaction mixture was filtered, and the filtrate was concentrated. The residue which contained p-nitrobenzyl (1R, 5R, 6S)-6-[(R)-1-tert-butyldimethylsilyloxyethyl]- 1-methyl-2-oxo-1-carba-2-penem-3-carboxylate was dissolved in 2 ml of acetonitrile, and 44 µl of diphenyl chlorophosphate (0.212 mmole) and 37 µl of diisopropylethylamine (0.212 mmole) were added thereto under ice-cooling, and the resultant mixture was stirred for 50 minutes. The reaction mixture was diluted with ethyl acetate, and washed each once with diluted hydrochloric acid, 5% aqueous sodium bicarbonate, and brine. Then, the organic phase was dried over anhydrous sodium sulfate, and concentrated. The residue was purified by chromatography (using toluene: ethyl acetate=10:1 as an eluent) to yield 50 mg of compound 6 as colorless foam (40%).

Compound 6: $^1$H-NMR (CDCl$_3$) δ: 8.2–8.1 (2H, m), 7.6–7.15 (12H, m), 5.33, 5.23 (2H, ABq, J=13.6Hz), 4.32–4.15 (1H, m), 4.19 (1H, dd, J=3.0Hz, 7.6Hz), 3.54–3.34 (1H, m), 3.28 (1H, dd, J=3.0Hz, 5.7Hz), 1.23 (3H, d, J=6Hz), 1.20 (3H, d, J=6Hz), 0.86 (9H, s), 0.07 (3H, s), 0.06 (3H, s).

EXAMPLE 8

The same compound as that in Example 7

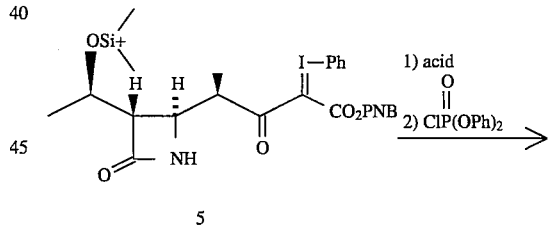

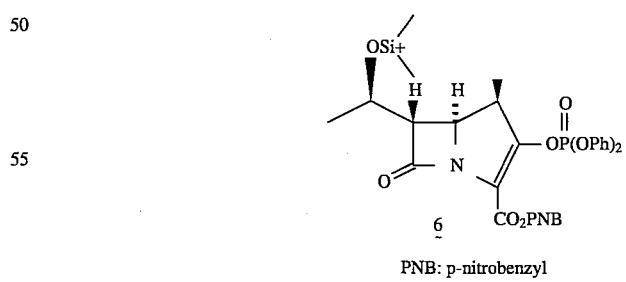

PNB: p-nitrobenzyl

A similar procedure to that in Example 2 to 5 in which an acid was used as a catalyst was conducted using compound 5 as a starting material. Then, a similar procedure to that in the step II in Example 7 was conducted.

The NMR and IR data are the same as those of Example 7.

EXAMPLE 9 p-Nitrobenzyl (1R, 5R, 6S)-6-[(R)-1-hydroxyethyl]-1-methyl-2-oxo-1-carbapenam-3-carboxylate (compound 13)

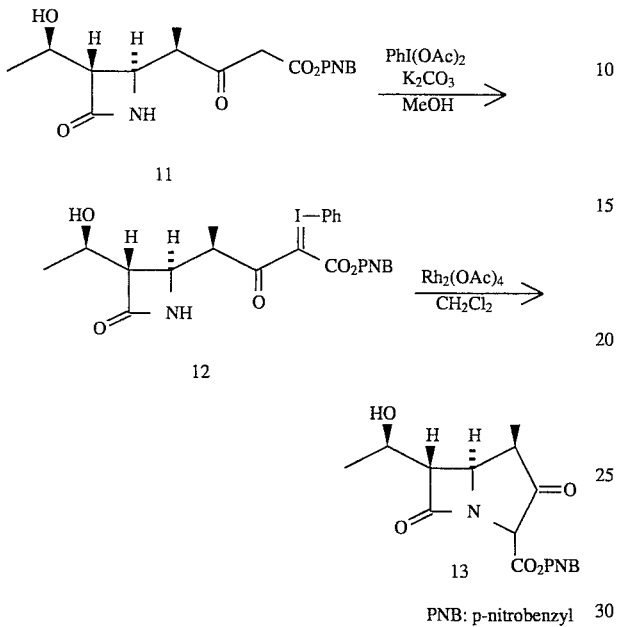

PNB: p-nitrobenzyl

To the solution which had been prepared by dissolving 200 mg of compound 12 obtained above (0.353 mmole) in 6 ml of dichloromethane, was added 1.6 mg of rhodium acetate (0.0036 mmole), and the mixture was stirred at room temperature for 20 minutes. The reaction mixture was diluted with dichloromethane, and the dilution was washed once with water, and once with brine. This is dried over anhydrous sodium sulfate, and concentrated. The residue was purified by chromatography over silica gel eluting with toluene:ethyl acetate:acetic acid=250:250:1, to yield 107 mg of compound 13 as colorless foam (84%), which contained 5% 1-α isomer resulting from this chromatography.

Compound 13

$^1$H-NMR (CDCl$_3$) δ 8.24 (2H, d, J=8.6Hz), 7.54 (2H, d, J=8.6Hz), 5.34 and 5.27 (2H, ABq, J=13.3Hz), 4.75 (1H, s), 4.34 (1H, quintet, J=6.5Hz), 4.25 (1H, dd, J=2.2Hz, 7.8Hz), 3.28 (1H, dd, J=2.2Hz, 6.5Hz), 2.84 (1H, quintet, J=7.8Hz), 1.39 (3H, d, J=6.5Hz), 1.23 (3H, d, J=7.8Hz). IR (CHCl$_3$) cm$^{-1}$: 3590, 3500 (br), 1760, 1605, 1523, 1455, 1375, 1345.

EXAMPLE 10

The same compound as that of Example 8

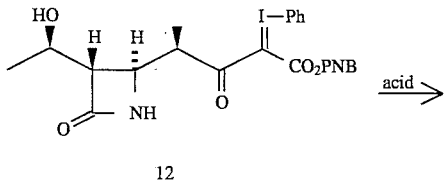

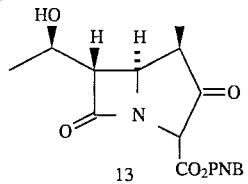

A similar procedure to that in Examples 2 to 5 in which an acid was used as a catalyst was conducted to give the title compound 13.

The NMR and IR data are the same as those of Example 9.

What is claimed is:

1. A process for preparing a β-lactam compound of the formula (I):

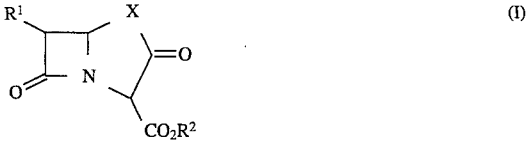

in which R$^1$ is hydrogen, alkyl which is optionally substituted by halogen or hydroxy which may be substituted by a hydroxy-protecting group, or amino which is optionally substituted by an amino-protecting group;

R$^2$ is a carboxy-protecting group; and

X is —SCH$_2$—, —OCH$_2$—, —CH$_2$CH$_2$—, or C$_n$H$_{2n+1}$CH═ (n=0–5), each of which is optionally substituted by lower alkyl, lower alkoxy, lower alkylthio, aryl, or lower alkenyl;

which comprises cyclization of an azetidinone derivative of the formula:

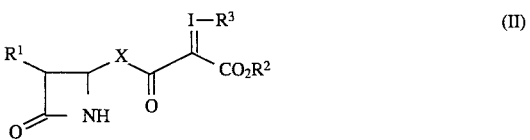

wherein R$^1$, R$^2$, and X are as defined above, and R$^3$ is aryl which is optionally substituted by halogen, lower alkyl, lower alkoxy, hydroxy, amino, or nitro, in the presence of a catalyst.

2. The process of claim 1 in which the azetidinone derivative is prepared by reacting a compound of the formula (III):

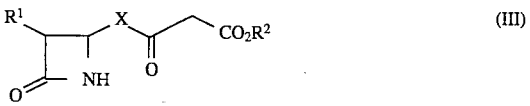

wherein R$^1$ is hydrogen, alkyl which is optionally substituted by halogen or hydroxy which may be substituted by a hydroxy-protecting group, or amino which is optionally substituted by an amino-protecting group;

R$^2$ is a carboxy-protecting group; and

X is —SCH$_2$—, —OCH$_2$—, —CH$_2$CH$_2$—, or C$_n$H$_{2n+1}$CH═ (n=0–5), each of which is optionally substituted by lower alkyl, lower alkoxy, lower alkylthio, aryl, or lower alkenyl;

with a compound of the formula:

R$^3$—I(Q)$_2$ wherein R³ is aryl which is optionally substituted by halogen, lower alkyl, lower alkoxy, hydroxy, amino, or nitro, and Q is a substituent derived from an anion part of an acid.

3. The process of claim 1 in which R³ is phenyl, and Q is acetyloxy.

4. The process of claim 2 in which R³ is phenyl, and Q is acetyloxy.

5. The process of claim 1 in which X is —SCH₂—, —OCH₂—, —CH₂CH₂—, or CH₃CH=.

6. The process of claim 2 in which X is —SCH₂—, —OCH₂—, —CH₂CH₂—, or CH₃CH=.

7. The process of claim 1 in which the catalyst is a salt of transition metal.

8. The process of claim 1 in which the catalyst is rhodium salt.

9. The process of claim 1 in which the catalyst is an acid.

10. The process of claim 2 in which the catalyst is an acid.

* * * * *